United States Patent
Pacetti et al.

(10) Patent No.: US 7,481,835 B1
(45) Date of Patent: Jan. 27, 2009

(54) ENCAPSULATED COVERED STENT

(75) Inventors: Stephen Dirk Pacetti, San Jose, CA (US); Hung Manh Le, San Jose, CA (US); Anthony Andreacchi, San Jose, CA (US); Manish Gada, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 463 days.

(21) Appl. No.: 10/976,550

(22) Filed: Oct. 29, 2004

(51) Int. Cl.
*A61F 2/06* (2006.01)

(52) U.S. Cl. .................................... 623/1.15; 623/901

(58) Field of Classification Search ................. 623/901, 623/1.11–1.16
See application file for complete search history.

(56) References Cited

U.S. PATENT DOCUMENTS

| | | | | |
|---|---|---|---|---|
| 2,072,303 A | 3/1937 | Herrmann et al. | ........ | 128/335.5 |
| 2,386,454 A | 10/1945 | Frosch et al. | ................. | 260/78 |
| 3,773,737 A | 11/1973 | Goodman et al. | ............. | 260/78 |
| 3,849,514 A | 11/1974 | Gray, Jr. et al. | ............. | 260/857 |
| 4,226,243 A | 10/1980 | Shalaby et al. | ........... | 128/335.5 |
| 4,329,383 A | 5/1982 | Joh | ............................. | 428/36 |
| 4,343,931 A | 8/1982 | Barrows | ..................... | 528/291 |
| 4,529,792 A | 7/1985 | Barrows | ..................... | 528/291 |
| 4,611,051 A | 9/1986 | Hayes et al. | ............. | 528/295.3 |
| 4,656,242 A | 4/1987 | Swan et al. | ............... | 528/295.3 |
| 4,733,665 A | 3/1988 | Palmaz | ....................... | 128/343 |
| 4,800,882 A | 1/1989 | Gianturco | ................... | 128/343 |
| 4,882,168 A | 11/1989 | Casey et al. | ................. | 424/468 |
| 4,886,062 A | 12/1989 | Wiktor | ....................... | 128/343 |
| 4,931,287 A | 6/1990 | Bae et al. | .................... | 424/484 |
| 4,941,870 A | 7/1990 | Okada et al. | .................. | 600/36 |
| 4,977,901 A | 12/1990 | Ofstead | ..................... | 128/772 |
| 5,019,096 A | 5/1991 | Fox, Jr. et al. | .................. | 623/1 |
| 5,100,992 A | 3/1992 | Cohn et al. | ................. | 424/501 |
| 5,112,457 A | 5/1992 | Marchant | ..................... | 204/165 |
| 5,133,742 A | 7/1992 | Pinchuk | ......................... | 623/1 |
| 5,163,952 A | 11/1992 | Froix | ............................. | 623/1 |
| 5,165,919 A | 11/1992 | Sasaki et al. | ................ | 424/488 |
| 5,219,980 A | 6/1993 | Swidler | ..................... | 528/272 |
| 5,258,020 A | 11/1993 | Froix | ............................. | 623/1 |
| 5,272,012 A | 12/1993 | Opolski | ................... | 428/423.1 |
| 5,292,516 A | 3/1994 | Viegas et al. | ................ | 424/423 |
| 5,298,260 A | 3/1994 | Viegas et al. | ................ | 424/486 |

(Continued)

FOREIGN PATENT DOCUMENTS

| | | |
|---|---|---|
| DE | 42 24 401 | 1/1994 |
| EP | 0 301 856 | 2/1989 |
| EP | 0 396 429 | 11/1990 |
| EP | 0 514 406 | 11/1992 |

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—Suzette J Gherbi
(74) *Attorney, Agent, or Firm*—Squire, Sanders & Dempsey, L.L.P.

(57) ABSTRACT

This disclosure provides a description of medical devices with polymeric cobwebbing disposed near the surfaces of the medical device. This cobwebbing can contain drug(s) and can enhance the mechanical and chemical function of intraluminal stents. Methods of using these devices and methods of preparing the devices are disclosed, as well.

18 Claims, 5 Drawing Sheets

U.S. PATENT DOCUMENTS

| | | | | |
|---|---|---|---|---|
| 5,300,295 A | 4/1994 | Viegas et al. ............... 424/427 |
| 5,306,501 A | 4/1994 | Viegas et al. ............... 424/423 |
| 5,306,786 A | 4/1994 | Moens et al. ............... 525/437 |
| 5,328,471 A | 7/1994 | Slepian ...................... 604/101 |
| 5,330,768 A | 7/1994 | Park et al. .................. 424/501 |
| 5,380,299 A | 1/1995 | Fearnot et al. ............. 604/265 |
| 5,417,981 A | 5/1995 | Endo et al. ................. 424/486 |
| 5,447,724 A | 9/1995 | Helmus et al. ............. 424/426 |
| 5,455,040 A | 10/1995 | Marchant .................... 424/426 |
| 5,462,990 A | 10/1995 | Hubbell et al. ............ 525/54.1 |
| 5,464,650 A | 11/1995 | Berg et al. ................... 427/2.3 |
| 5,485,496 A | 1/1996 | Lee et al. ..................... 378/64 |
| 5,516,881 A | 5/1996 | Lee et al. ................... 528/320 |
| 5,569,463 A | 10/1996 | Helmus et al. ............. 424/426 |
| 5,578,073 A | 11/1996 | Haimovich et al. ............ 623/1 |
| 5,584,877 A | 12/1996 | Miyake et al. .................. 623/1 |
| 5,605,696 A | 2/1997 | Eury et al. .................. 424/423 |
| 5,607,467 A | 3/1997 | Froix ............................. 623/1 |
| 5,609,629 A | 3/1997 | Fearnot et al. ................. 623/1 |
| 5,610,241 A | 3/1997 | Lee et al. ................... 525/411 |
| 5,616,338 A | 4/1997 | Fox, Jr. et al. ............... 424/423 |
| 5,624,411 A | 4/1997 | Tuch .......................... 604/265 |
| 5,628,730 A | 5/1997 | Shapland et al. ............. 604/21 |
| 5,644,020 A | 7/1997 | Timmermann et al. ...... 528/288 |
| 5,649,977 A | 7/1997 | Campbell ...................... 623/1 |
| 5,658,995 A | 8/1997 | Kohn et al. ................. 525/432 |
| 5,667,767 A | 9/1997 | Greff et al. ................ 424/9.411 |
| 5,670,558 A | 9/1997 | Onishi et al. ............... 523/112 |
| 5,674,242 A | 10/1997 | Phan et al. .................. 606/198 |
| 5,679,400 A | 10/1997 | Tuch .......................... 427/2.14 |
| 5,700,286 A | 12/1997 | Tartaglia et al. ................ 623/1 |
| 5,702,754 A | 12/1997 | Zhong ........................ 427/2.12 |
| 5,711,958 A | 1/1998 | Cohn et al. ................. 424/423 |
| 5,716,981 A | 2/1998 | Hunter et al. .............. 514/449 |
| 5,721,131 A | 2/1998 | Rudolph et al. ............. 435/240 |
| 5,723,219 A | 3/1998 | Kolluri et al. ............. 428/411.1 |
| 5,735,897 A | 4/1998 | Buirge ........................ 623/12 |
| 5,746,998 A | 5/1998 | Torchilin et al. ............ 424/9.4 |
| 5,759,205 A | 6/1998 | Valentini ..................... 623/16 |
| 5,776,184 A | 7/1998 | Tuch ............................. 623/1 |
| 5,783,657 A | 7/1998 | Pavlin et al. ................ 528/310 |
| 5,788,979 A | 8/1998 | Alt et al. ..................... 424/426 |
| 5,800,392 A | 9/1998 | Racchini ...................... 604/96 |
| 5,820,917 A | 10/1998 | Tuch ............................ 427/2.1 |
| 5,824,048 A | 10/1998 | Tuch ............................. 623/1 |
| 5,824,049 A | 10/1998 | Ragheb et al. .................. 623/1 |
| 5,830,178 A | 11/1998 | Jones et al. .................. 604/49 |
| 5,837,008 A | 11/1998 | Berg et al. ..................... 623/1 |
| 5,837,313 A | 11/1998 | Ding et al. ................. 427/2.21 |
| 5,849,859 A | 12/1998 | Acemoglu ................... 528/271 |
| 5,851,508 A | 12/1998 | Greff et al. ................ 424/9.411 |
| 5,854,376 A | 12/1998 | Higashi ...................... 528/288 |
| 5,858,746 A | 1/1999 | Hubbell et al. ............. 435/177 |
| 5,865,814 A | 2/1999 | Tuch .......................... 604/265 |
| 5,869,127 A | 2/1999 | Zhong ........................ 427/2.12 |
| 5,873,904 A | 2/1999 | Ragheb et al. .................. 623/1 |
| 5,876,433 A | 3/1999 | Lunn ............................. 623/1 |
| 5,877,224 A | 3/1999 | Brocchini et al. ......... 514/772.2 |
| 5,879,713 A | 3/1999 | Roth et al. .................. 424/489 |
| 5,902,875 A | 5/1999 | Roby et al. ................. 528/310 |
| 5,905,168 A | 5/1999 | Dos Santos et al. ......... 562/590 |
| 5,910,564 A | 6/1999 | Gruning et al. ............. 528/310 |
| 5,914,387 A | 6/1999 | Roby et al. ................. 528/310 |
| 5,919,893 A | 7/1999 | Roby et al. ................. 525/411 |
| 5,925,720 A | 7/1999 | Kataoka et al. ............. 525/523 |
| 5,932,299 A | 8/1999 | Katoot ........................ 427/508 |
| 5,955,509 A | 9/1999 | Webber et al. ............ 514/772.7 |
| 5,958,385 A | 9/1999 | Tondeur et al. ............... 424/61 |
| 5,962,138 A | 10/1999 | Kolluri et al. ............. 428/411.1 |
| 5,971,954 A | 10/1999 | Conway et al. .............. 604/96 |
| 5,980,928 A | 11/1999 | Terry .......................... 424/427 |
| 5,980,972 A | 11/1999 | Ding .......................... 427/2.24 |
| 5,997,517 A | 12/1999 | Whitbourne ................ 604/265 |
| 6,010,530 A | 1/2000 | Goicoechea .................... 623/1 |
| 6,011,125 A | 1/2000 | Lohmeijer et al. ........... 525/440 |
| 6,015,541 A | 1/2000 | Greff et al. .................. 424/1.25 |
| 6,033,582 A | 3/2000 | Lee et al. ...................... 216/37 |
| 6,034,204 A | 3/2000 | Mohr et al. ................. 528/328 |
| 6,042,875 A | 3/2000 | Ding et al. .................. 427/2.24 |
| 6,051,576 A | 4/2000 | Ashton et al. ............... 514/255 |
| 6,051,648 A | 4/2000 | Rhee et al. .................. 525/54.1 |
| 6,054,553 A | 4/2000 | Groth et al. ................. 528/335 |
| 6,056,993 A | 5/2000 | Leidner et al. ............. 427/2.25 |
| 6,060,451 A | 5/2000 | DiMaio et al. ................ 514/13 |
| 6,060,518 A | 5/2000 | Kabanov et al. ............. 514/781 |
| 6,080,488 A | 6/2000 | Hostettler et al. ......... 428/423.3 |
| 6,096,070 A | 8/2000 | Ragheb et al. .................. 623/1 |
| 6,099,562 A | 8/2000 | Ding et al. .................. 623/1.46 |
| 6,110,188 A | 8/2000 | Narciso, Jr. ................. 606/153 |
| 6,110,483 A | 8/2000 | Whitbourne et al. ........ 424/423 |
| 6,113,629 A | 9/2000 | Ken ............................. 623/1.1 |
| 6,120,491 A | 9/2000 | Kohn et al. ................. 604/502 |
| 6,120,536 A | 9/2000 | Ding et al. .................. 623/1.43 |
| 6,120,788 A | 9/2000 | Barrows ...................... 424/426 |
| 6,120,904 A | 9/2000 | Hostettler et al. ......... 428/423.3 |
| 6,121,027 A | 9/2000 | Clapper et al. .............. 435/180 |
| 6,129,761 A | 10/2000 | Hubbell ....................... 623/11 |
| 6,136,333 A | 10/2000 | Cohn et al. ................. 424/423 |
| 6,143,354 A | 11/2000 | Koulik et al. .............. 427/2.24 |
| 6,153,252 A | 11/2000 | Hossainy et al. ............. 427/2.3 |
| 6,159,978 A | 12/2000 | Myers et al. .............. 514/252.1 |
| 6,165,212 A | 12/2000 | Dereume et al. ........... 623/1.13 |
| 6,172,167 B1 | 1/2001 | Stapert et al. ............... 525/420 |
| 6,177,523 B1 | 1/2001 | Reich et al. ................. 525/459 |
| 6,180,632 B1 | 1/2001 | Myers et al. .............. 514/252.1 |
| 6,203,551 B1 | 3/2001 | Wu ............................. 606/108 |
| 6,211,249 B1 | 4/2001 | Cohn et al. ................ 514/772.1 |
| 6,214,901 B1 | 4/2001 | Chudzik et al. ............. 523/113 |
| 6,231,600 B1 | 5/2001 | Zhong ........................ 623/1.42 |
| 6,240,616 B1 | 6/2001 | Yan ............................ 29/527.2 |
| 6,245,753 B1 | 6/2001 | Byun et al. .................... 514/56 |
| 6,245,760 B1 | 6/2001 | He et al. ................... 514/234.8 |
| 6,248,129 B1 | 6/2001 | Froix ......................... 623/1.42 |
| 6,251,136 B1 | 6/2001 | Guruwaiya et al. ........ 623/1.46 |
| 6,254,632 B1 | 7/2001 | Wu et al. ................... 623/1.15 |
| 6,258,121 B1 | 7/2001 | Yang et al. ................. 623/1.46 |
| 6,258,371 B1 | 7/2001 | Koulik et al. ............... 424/422 |
| 6,262,034 B1 | 7/2001 | Mathiowitz et al. .......... 514/44 |
| 6,270,788 B1 | 8/2001 | Koulik et al. ............... 424/423 |
| 6,277,449 B1 | 8/2001 | Kolluri et al. ............... 427/289 |
| 6,283,947 B1 | 9/2001 | Mirzaee ...................... 604/264 |
| 6,283,949 B1 | 9/2001 | Roorda ................... 604/288.02 |
| 6,284,305 B1 | 9/2001 | Ding et al. .................. 427/2.28 |
| 6,287,628 B1 | 9/2001 | Hossainy et al. ............. 427/2.3 |
| 6,299,604 B1 | 10/2001 | Ragheb et al. .............. 604/265 |
| 6,306,176 B1 | 10/2001 | Whitbourne ............. 623/23.59 |
| 6,331,313 B1 | 12/2001 | Wong et al. ................. 424/427 |
| 6,335,029 B1 | 1/2002 | Kamath et al. .............. 424/423 |
| 6,344,035 B1 | 2/2002 | Chudzik et al. ............. 604/265 |
| 6,346,110 B2 | 2/2002 | Wu ............................. 606/108 |
| 6,358,556 B1 | 3/2002 | Ding et al. .................. 427/2.24 |
| 6,379,381 B1 | 4/2002 | Hossainy et al. ........... 623/1.42 |
| 6,387,379 B1 | 5/2002 | Goldberg et al. ............ 424/400 |
| 6,395,326 B1 | 5/2002 | Castro et al. ................ 427/2.24 |
| 6,419,692 B1 | 7/2002 | Yang et al. ................. 623/1.15 |
| 6,451,373 B1 | 9/2002 | Hossainy et al. ........... 427/2.25 |
| 6,475,234 B1 * | 11/2002 | Richter et al. .............. 623/1.15 |
| 6,482,834 B2 | 11/2002 | Spada et al. ................. 514/311 |
| 6,494,862 B1 | 12/2002 | Ray et al. ................. 604/96.01 |
| 6,503,538 B1 | 1/2003 | Chu et al. .................... 424/497 |
| 6,503,556 B2 | 1/2003 | Harish et al. ............... 427/2.24 |
| 6,503,954 B1 | 1/2003 | Bhat et al. ................. 514/772.2 |
| 6,506,437 B1 | 1/2003 | Harish et al. ............... 427/2.25 |
| 6,524,347 B1 | 2/2003 | Myers et al. |

| Patent/Pub. No. | Date | Inventor | Class |
|---|---|---|---|
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | 214/311 |
| 6,530,950 B1 | 3/2003 | Alvarado et al. | 623/1.13 |
| 6,530,951 B1 | 3/2003 | Bates et al. | 623/1.45 |
| 6,540,776 B2 | 4/2003 | Sanders Millare et al. | 623/1.15 |
| 6,544,223 B1 | 4/2003 | Kokish | 604/103.1 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B2 | 7/2003 | Jackson et al. | 623/1.15 |
| 6,585,765 B1 | 7/2003 | Hossainy et al. | 623/1.45 |
| 6,585,765 B1 | 7/2003 | Mirzaee | 264/400 |
| 6,605,154 B1 | 8/2003 | Villareal | 118/500 |
| 6,616,765 B1 | 9/2003 | Castro et al. | 623/1.45 |
| 6,623,448 B2 | 9/2003 | Slater | 604/95.01 |
| 6,625,486 B2 | 9/2003 | Lundkvist et al. | 604/21 |
| 6,645,135 B1 | 11/2003 | Bhat | 600/3 |
| 6,645,195 B1 | 11/2003 | Bhat et al. | 604/528 |
| 6,656,216 B1 | 12/2003 | Hossainy et al. | 623/1.13 |
| 6,656,506 B1 | 12/2003 | Wu et al. | 424/489 |
| 6,660,034 B1 | 12/2003 | Mandrusov et al. | 623/1.42 |
| 6,663,662 B2 | 12/2003 | Pacetti et al. | 623/1.13 |
| 6,663,880 B1 | 12/2003 | Roorda et al. | 424/423 |
| 6,666,880 B1 | 12/2003 | Chiu et al. | 623/1.11 |
| 6,673,154 B1 | 1/2004 | Pacetti et al. | 118/500 |
| 6,673,385 B1 | 1/2004 | Ding et al. | 427/2.24 |
| 6,689,099 B2 | 2/2004 | Mirzaee | 604/107 |
| 6,695,920 B1 | 2/2004 | Pacetti et al. | 118/500 |
| 6,706,013 B1 | 3/2004 | Bhat et al. | 604/96.01 |
| 6,709,514 B1 | 3/2004 | Hossainy | 118/52 |
| 6,712,845 B2 | 3/2004 | Hossainy | 623/1.42 |
| 6,713,119 B2 | 3/2004 | Hossainy et al. | 427/2.25 |
| 6,716,444 B1 | 4/2004 | Castro et al. | 424/422 |
| 6,723,120 B2 | 4/2004 | Yan | 623/1.15 |
| 6,733,768 B2 | 5/2004 | Hossainy et al. | 424/426 |
| 6,740,040 B1 | 5/2004 | Mandrusov et al. | 600/439 |
| 6,743,462 B1 | 6/2004 | Pacetti | 427/2.24 |
| 6,749,626 B1 | 6/2004 | Bhat et al. | 623/1.1 |
| 6,753,071 B1 | 6/2004 | Pacetti | 428/212 |
| 6,758,859 B1 | 7/2004 | Dang et al. | 623/1.15 |
| 6,759,054 B2 | 7/2004 | Chen et al. | 424/423 |
| 6,764,505 B1 | 7/2004 | Hossainy et al. | 623/1.15 |
| 6,770,089 B1 * | 8/2004 | Hong et al. | 623/1.16 |
| 6,939,376 B2 * | 9/2005 | Shulze et al. | 623/1.42 |
| 2001/0007083 A1 | 7/2001 | Roorda | 623/1.15 |
| 2001/0014717 A1 | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0029351 A1 | 10/2001 | Falotico et al. | 604/103.02 |
| 2001/0037145 A1 | 11/2001 | Guruwaiya et al. | 623/1.15 |
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0009604 A1 | 1/2002 | Zamora et al. | 428/450 |
| 2002/0016625 A1 | 2/2002 | Falotico et al. | 623/1.13 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.37 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1 | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1 | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0109917 A1 * | 6/2003 | Rudin et al. | 623/1.15 |
| 2003/0113439 A1 | 6/2003 | Pacetti et al. | 427/2.24 |
| 2003/0124279 A1 * | 7/2003 | Sridharan et al. | 428/35.7 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096504 A1 | 5/2004 | Michal | 424/471 |
| 2004/0098117 A1 | 5/2004 | Hossainy et al. | 623/1.42 |

FOREIGN PATENT DOCUMENTS

| | | |
|---|---|---|
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |

| | | |
|---|---|---|
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis($\alpha$-amino acid)$\alpha$,$\omega$-Alkylene Diesters, and Aliphatic Dicarbolic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of Polymers in improving the results of stenting in coronary arteries*, Biomaterials 17:685-694 (1996).

Saotome, et al., *Novel Enzymatically Degradable Polymers Comprising $\alpha$-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a soild tumor*, Journal of Controlled Release 50:79-92 (1998).

* cited by examiner

ENCAPSULATED COVERED STENT

DESCRIPTION OF THE BACKGROUND

Physicians commonly treat blood vessel occlusions by mechanically enhancing blood flow in the affected vessels, such as by employing a stent. Stents act as scaffoldings, physically holding open and, if desired, expanding the wall of affected vessels. Typically, stents can compress for insertion through small lumens via catheters and then expand to a larger diameter once they are positioned. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Physicians also use stents for providing biological therapy by medicating the stents. Medicated stents allow local administration of a drug. This is preferred because these stents concentrate the drug at a specific site and thus deliver smaller total medication levels in comparison to systemic dosages.

One stent medicating method involves using a coating of a polymeric carrier on the stent. Coating comprises immersing the stent in, rolling the material on, applying the material to, or spraying the stent with a material including a solvent, a polymer dissolved in the solvent, and a therapeutic substance dispersed in the solvent. Then the solvent evaporates, leaving a polymer and drug coating. After stent implantation, the stent releases the drug in a sustained manner.

U.S. Pat. No. 6,139,573, Sogard et al. teaches an elongated, radially expandable, tubular stent and a polymeric layer covering and conforming to its surface. It teaches laminating a polymeric liner layer and an external polymer layer together to form a composite structure, containing the stent, and at least three domains of distinct porosity. It teaches making the stent from a variety of materials including stainless steel, titanium, platinum, gold, or other biocompatible metals. Furthermore, it teaches that the polymeric layers are expanded polytetrafluoroethylene (ePTFE).

In U.S. Pat. No. 6,010,530, Goicoechea teaches a self-expanding stent encapsulated by a skin. The stent contains a continuous, zigzag, nitinol wire wound into several concentric hoops. Its skin is an elastomeric polymer, such as Chronoflex (available from Poly-Medica Biomaterials Inc., Woburn, Mass.).

In U.S. Pat. No. 5,749,880, Banas et al. teach an encapsulated stent that comprises at least one stent member concentrically interdisposed between at least two tubular ePTFE extrudates, each of the extrudates have a uniaxial fibril microstructure oriented parallel to the longitudinal axis of the stent.

United States Patent Application Publication No. US 2002/0133224 A1 discloses a stent encapsulated with a microporous polymeric membrane. An electrostatic deposition process provides stent encapsulation.

Current stents have an overall cylindrical shape with a complex pattern of struts. When placed in the target vessel and expanded, the stent occupies about 10-25% of the vessel wall surface area. Stents are an unusual medical device in that their design is a compromise between mechanical function and biological impact. Skilled Artisans want stents to mechanically support the vessel. This argues for high wall coverage to give good scaffolding, stopping all plaque prolapse. But since stents can cause biological responses that precipitate in-stent restenosis, or thrombosis skilled artisans want biologically invisible stents, which tends toward low wall coverage.

In addition to non-covered stents, covered stents are also known. Physicians use these devices for certain niche applications. These often serve as bailout devices in cases of severe dissection or perforation of the arterial wall. They are also used to treat aneurysms that may form in the vessel wall from disease or trauma. Their mechanical limitations center on their deliverability and larger profile compared to regular stents. Biological challenges include not only restenosis, but also a higher incidence of thrombotic complications due to the larger surface area of synthetic material. But covered stents could deliver a higher drug payload, and deliver this drug more uniformly to the vessel wall. Between the arterial wall coverage of bare metal stents and that of fully covered stents, lies a continuum in the extent of vessel wall coverage. The best coverage is the minimum amount needed to accomplish the mechanical task without creating adverse biological responses.

There is a place for covered stents in interventional cardiology but they still have the following issues:

- The covering increases the stent profile because it lies on the stent's outer surfaces so it is external to the stent;
- The covering must expand with the stent; tearing is possible if the covering is not sufficiently elastic;
- Attachment of the covering to the stent is problematic; insecure attachment can lead to the covering becoming loose or folding over;
- A covered stent that is too impermeable can completely isolate the underlying endothelium/smooth muscle from its blood supply, which can cause tissue death or necrosis.

SUMMARY OF THE INVENTION

The current invention can be characterized as having embodiments of methods for making medical devices and devices made from those methods. The devices comprise an implantable portion, with cutouts in the implantable portion that create a lattice structure having sidewalls and a plurality of polymer filaments between the sidewalls or between separate portions of the same sidewall. In some embodiments, the filaments have an average diameter of 0.1 microns to 100 microns, or 0.2 microns to 80 microns, when the device is ready for delivery. In these or other embodiments, the average interfilament spacing is 0.2 microns to 50 microns, or 0.5 microns to 10 microns, when the device is ready for delivery.

Different invention embodiments exist in which different portions of the openings formed by the cutouts have different degrees of covering of or blocking of the openings. For example, embodiments in which the polymer filaments block 10-90 percent of the opening formed by the cutout portion are within the scope of the invention, as are embodiments with 20-80 percent or 30-70 percent blockage.

In some invention embodiments, the medical device is a stent, such as a self-expanding stent or a balloon expandable stent. The filaments can comprise drug(s), such as anti-proliferative, antineoplastic, antiinflammatory, antiplatelet, anticoagulant, antifibrin, antithrombin, antimitotic, antibiotic, or antioxidant substances, or their combinations. The drug(s) are coated or introduced into or onto the filaments after the filaments are formed or the filaments are prepared from solutions already containing the drug(s).

Certain processing parameters are modified to cause filament formation or cobwebbing between the sidewalls of the stent struts. These parameters include the solvent boiling point, the difference between the polymer solubility parameter and the solubility parameter for the trailing solvent, polymer concentration parameter, spray nozzle temperature parameter, drying nozzle temperature parameter, spray flow rate parameter, atomization pressure parameter, spray solution surface-tension parameter, polymer weight average molecular weight parameter, or their combinations.

Using solvents of lower boiling point such that the boiling point of the solvent is 25° C. to 165° C. provides an invention embodiment. Alternatively, the solvents boiling point is decreased such that the boiling point of the solvent is 40° C. to 100° C.

Other embodiments are provided by each of the following:

the difference in the Hildebrand solubility solvation parameter (solubility parameter) between the polymer and the trailing solvent is increased such that the difference in absolute value is 1 to 10 $(cal/cm^3)^{1/2}$, or 2 to 6 $(cal/cm^3)^{1/2}$.

the percent polymer in solution (w/w) is increased such that the solution has a concentration of 1 to 10%, or 2 to 6%.

the spray nozzle temperature is increased such that the spray nozzle temperature is 30° C. to 100° C., or 40° C. to 75° C.

the dry nozzle temperature is increased such that the dry nozzle temperature is ambient to 140° C., or 40° C. to 100° C.

the spray flow rate is increased such that the spray flow rate is 0.1 µg/mm sec to 2 µg/mm sec, or 0.2 µg/mm to 1.5 µg/mm sec. This flow rate is expressed as the µg of coating applied per millimeter of stent length per second.

the atomization pressure parameter is increased such that the atomization pressure is 10 psi to 50 psi, or 15 psi to 30 psi.

the surface-tension parameter is decreased such that the surface tension of the solution is 15 dyne/cm to 50 dyne/cm, or 18 dyne/cm to 35 dyne/cm.

the stent rotation parameter is increased such that the rotation speed of the stent is 10 RPM to 1000 RPM, or 60 RPM to 500 RPM.

In some embodiments, the stent is a self-expandable stent in its relaxed state before the coating step. In some embodiments, the stent is a balloon-expandable stent, and the stent is expanded to as large a degree as possible consistent with substantially returning the stent to the unexpanded state before the coating step.

DETAILED DESCRIPTION

Figure 1:
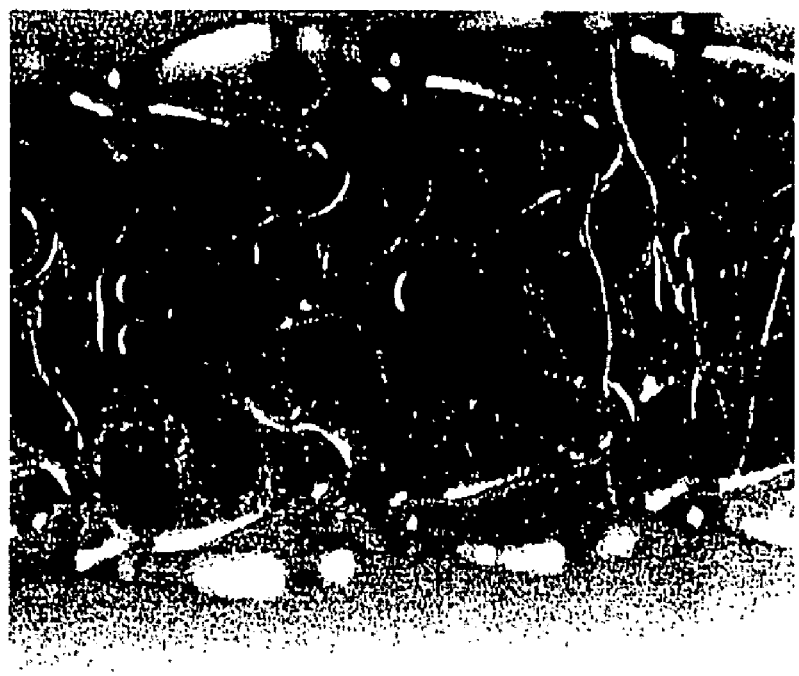
FIG. 1 is a photograph of a stent coated with a 2% (w/w) Kynar Flex 2800 polymer composition.
Figure 2:
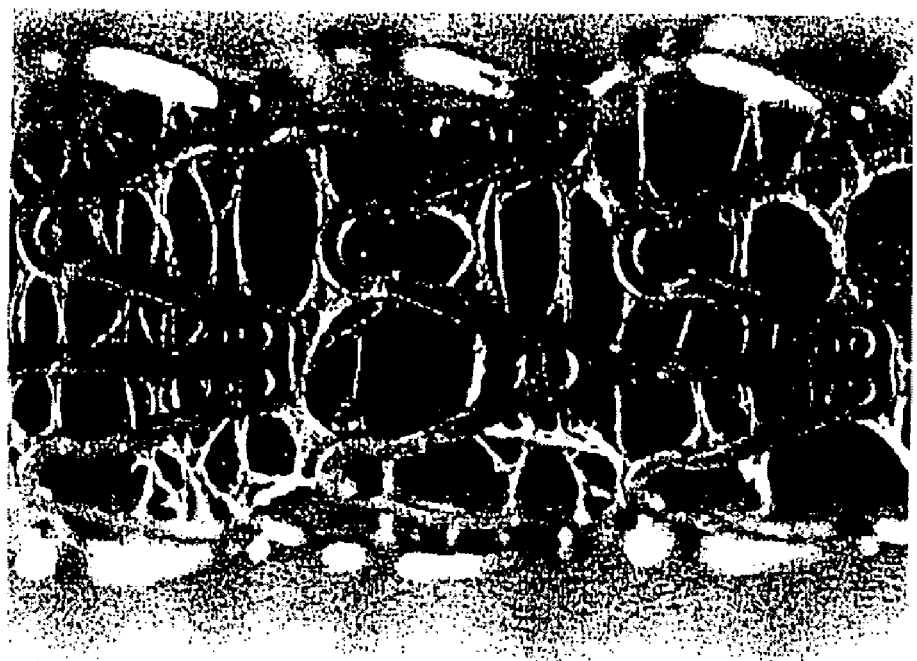
FIG. 2 is a photograph of a stent coated with a 2% (w/w) Solef 11010 polymer solution.

In one invention embodiment, a covered stent is formed using a spray process. By appropriately adjusting the spray process parameters, the polymer coating can be made to cobweb between the stent struts. This forms a structure akin to spunbonded, non-woven fabrics. FIG. 1 shows a stent in which fibers of Kynar have been caused to form between the stent struts. Similarly, FIG. 2 shows a stent in which fibers of Solef have been caused to form between the struts. Formation, in part, comes from rejecting standard process parameters, which are specifically chosen to minimize or avoid this cobwebbing effect.

Figure 3:
FIG. 3 is another photograph of a stent coated with a Kynar Flex 2800 polymer composition.
Figure 4:
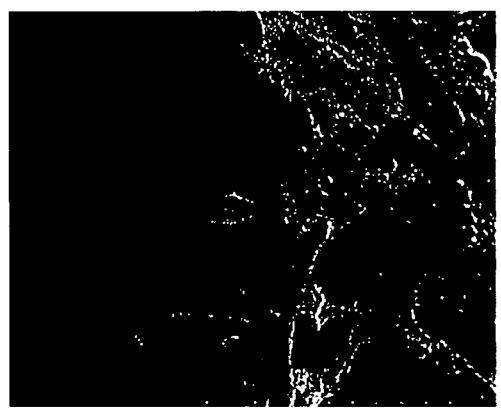
FIG. 4 is a close-up of the stent of FIG. 3.
Figure 5:
FIG. 5 is another close-up of the stent of FIG. 3.

A particular configuration for a covered stent and a means to make this construct by a spray process is disclosed. This covered stent is made using the phenomena of cobwebbing with stent coverage. Similar polymers can also be coated in a conformal way, without cobwebbing. Adjusting the process conditions can vary the degree of cobwebbing. One can go from a stent with low coverage to one that is completely covered. At the level of the struts 30, in FIG. 6, the coating 35 encapsulates the struts 30. The polymer strands, filaments, or cobwebs 40 emanate from the sidewalls 45, FIG. 7. FIG. 3 illustrates a stent with high coverage of Kynar Flex 2800. FIG. 4 and FIG. 5 show the highly covered Kynar Flex 2800 stent in close-up. Process parameter control can yield very fine polymer-fiber structure.

Figure 6:
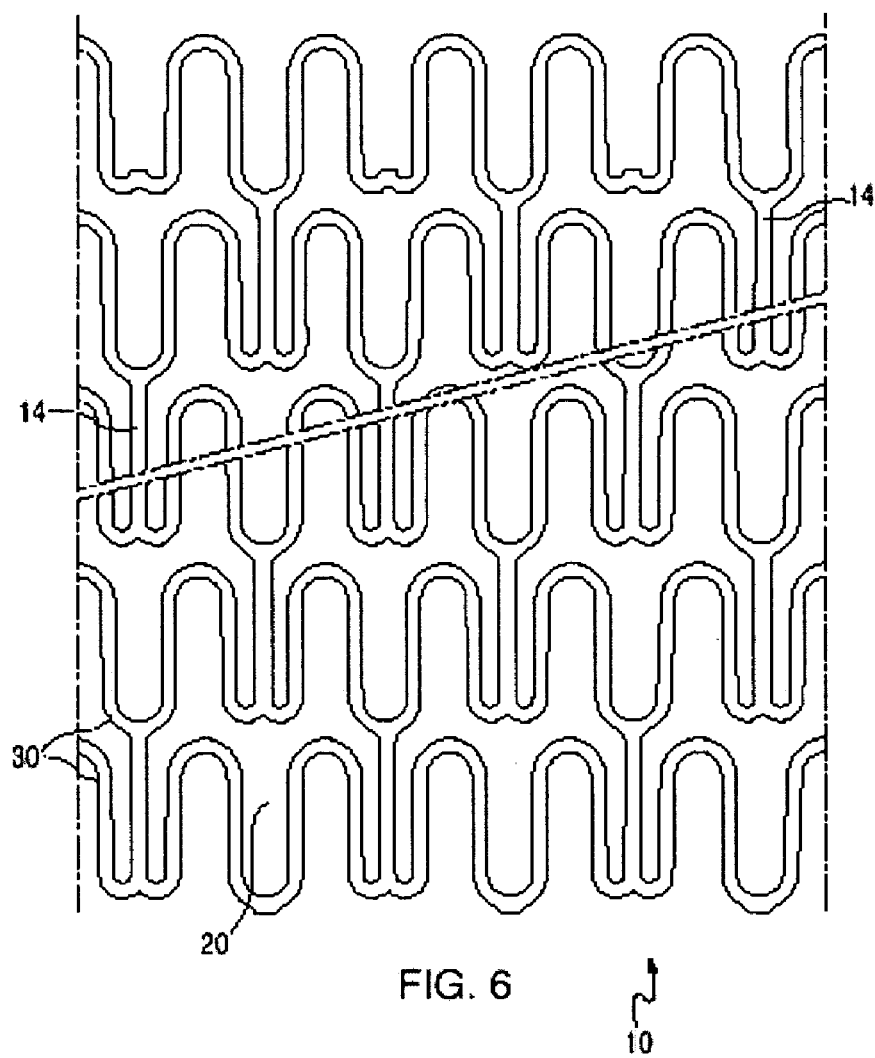
FIG. 6 illustrates a conventional stent.
Figure 7:
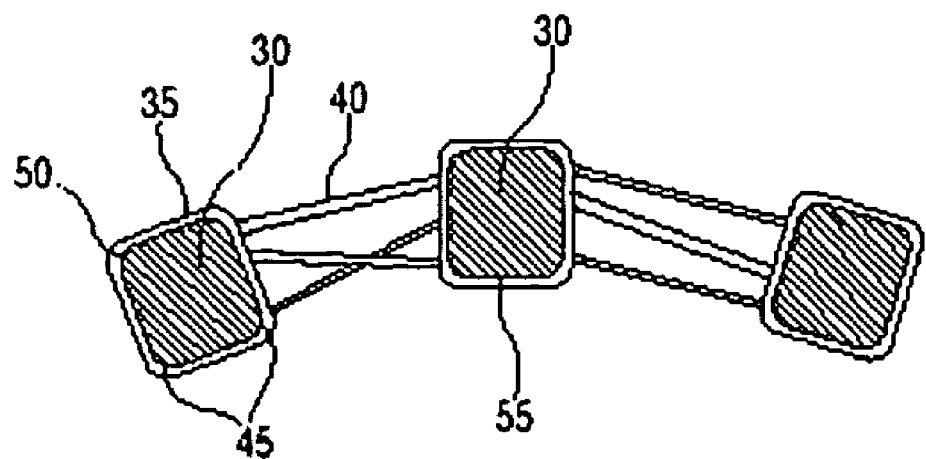
FIG. 7 illustrates an invention device in cross-section.

FIG. 6 illustrates a conventional stent 10 formed from a plurality of struts 30. The plurality of struts 30 are radially expandable and interconnected by connecting elements 14 that are disposed between adjacent struts 30, leaving lateral openings or cutouts 20 between adjacent struts 30. Struts 30 and connecting elements 14 define a tubular stent body having an outer, tissue-contacting surface and an inner surface. Although the embodiments of the present invention are described with reference to a stent, the application of the invention should not be limited to a stent and is equally applicable to other implantable medical devices.

Figure 8:
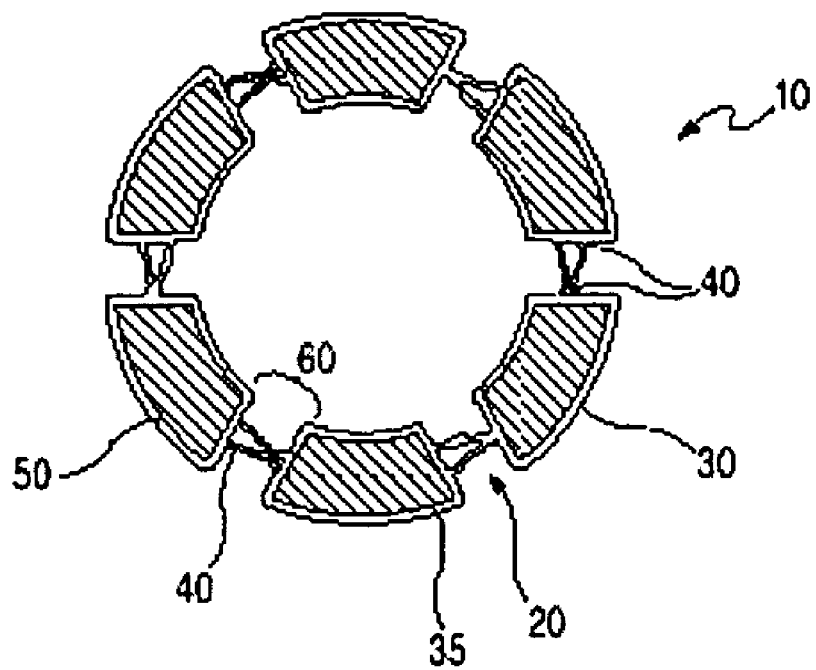
FIG. 8 illustrates an invention device in cross-section.
Figure 9:
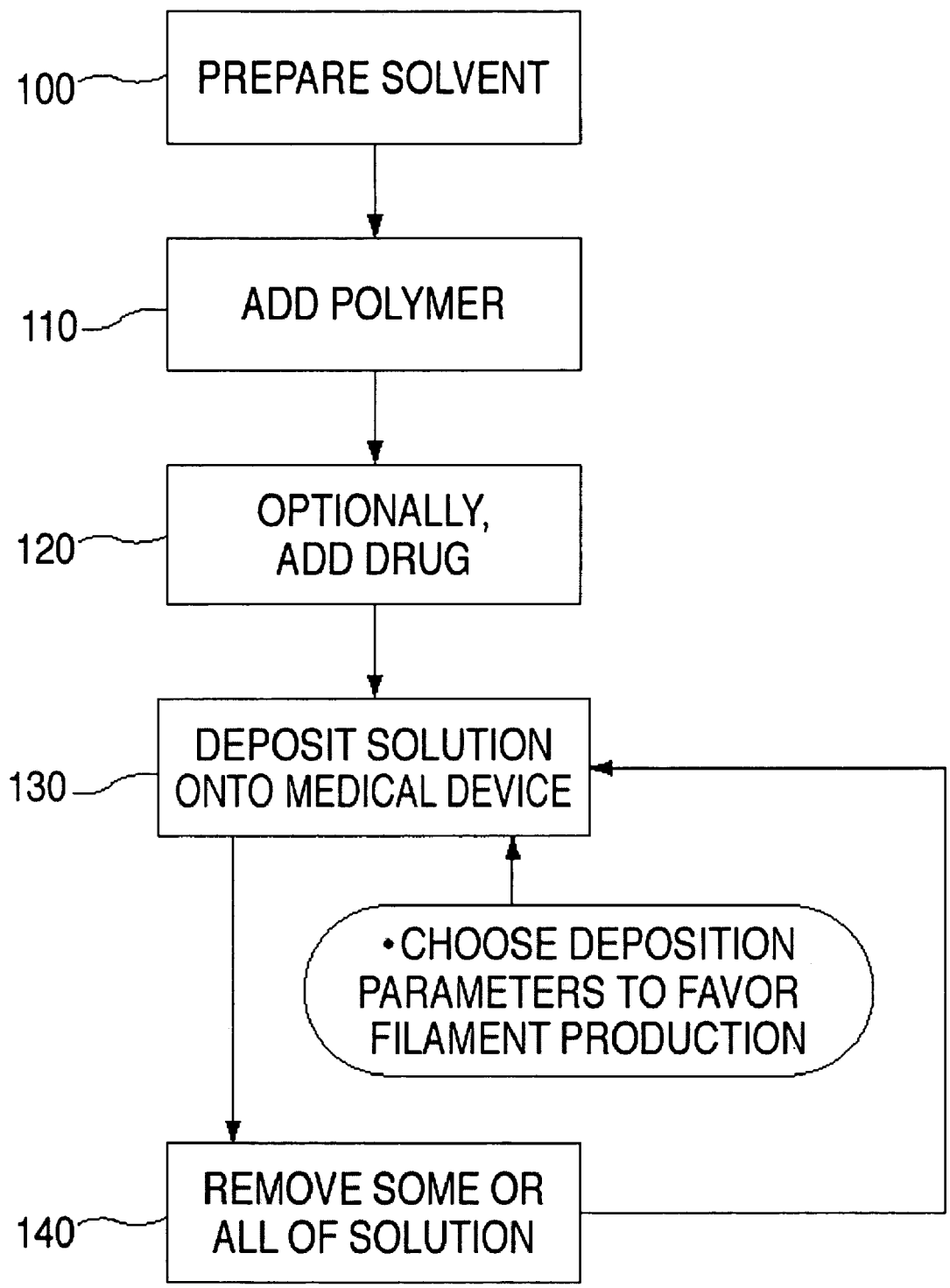
FIG. 9 is a schematic of a prototypical invention process.

FIG. 8 shows a stent 10 in cross-section (axial). Cutouts 20 allow passage from the outside of the stent 10 to the inside. Strut 30 is partially surrounded by cutouts 20, which have sidewalls 45. Invention coating processes coat the stent 10 in two ways. The conformal coating portion 35 acts as a typical conformal coating. And the webbed coating portion 60 comprises filaments 40 that extend from the conformal coating portion 35 on a sidewall 45 to the conformal coating portion 35 of a separate part of the sidewall 45 or to another sidewall.

In some embodiments, filaments 40 are substantially completely further inward than the surface 50. In some embodiments, filaments 40 occupy 10-90% of the areal space of cutouts 20. In other embodiments, filaments 40 occupy 20-80%, 30-70%, or 40-60% of the areal space of cutouts 20. For purposes of this disclosure, areal space is defined as the area of the cutout 20 measured at the surface 50. If filaments 40 occupy 50% of the areal space of cutouts 20, this means that filaments 40 block 50% of the space occupied by the cutout.

Portions of some embodiments of polymer filaments are less than 1 micron in diameter with interfilament spacings of 1-5 microns. These filaments and spacings are similar to those seen in ePTFE fabrics, which commonly compose stent covers. Generally, polymer filaments average from 0.1 microns to 100 microns; more narrowly, 0.2 microns to 80 microns or 0.5 microns to 20 microns. Also, the interfilament spacing generally averages from 0.2 microns to 50 microns; more narrowly, 0.5 microns to 25 microns or 0.5 microns to 10 microns.

Depending on the process parameters, the distribution of filament diameters can range from 0.1 microns to 100 microns, or 0.2 microns to 80 microns, or 0.5 microns to 20 microns. Likewise, the distribution of interfilament spacing can range from 0.2 microns to 50 microns, or 0.5 microns to 25 microns, or 0.5 microns to 10 microns.

Both filament diameter and interfilament spacing are measured in the unexpanded, ready-for-delivery state for self-expanding stents. These values are measured in the ready-fordelivery state for balloon expandable stents. "Ready for delivery" means that the medical device is completely manufactured, cleaned, packaged, etc. and could be implanted in a patient.

In one embodiment, the stent is coated in a collapsed configuration with the struts nearly touching. On expansion, the polymer between the struts, in this embodiment, is subjected to very high strains. The following methods can be used to reduce this strain.

- The self-expanding stent can be coated in the expanded state. When collapsed, the mesh covering accordions or folds up.
- For balloon expandable stents, the stent can be expanded as much as possible and then coated. This will reduce the degree of strain the polymer must accommodate.

Methods of Making

Current coating processes can create cobwebbing with a variety of polymers. For each material, those of ordinary skill in the art can determine the process parameters necessary for coating a medical device. Examples of categories of such process parameters and useful trends are as follows:

- Use solvents with higher volatility (this is referred to as a volatility parameter)
- Use trailing solvents that are poor solvents for the polymer (this is referred to as a solvation parameter)
- Increase the concentration of the polymer in the solvent (this is referred to as a concentration parameter)
- Increase the spray nozzle temperature (this is referred to as a spray nozzle parameter)
- Increase the dry nozzle temperature (this is referred to as a dry nozzle parameter)
- Increase the flow rate (this is referred to as a flow parameter)
- Increase the atomization pressure (this is referred to as a atomization pressure parameter)
- Increase the surface tension of the solution (This is referred to as a surface-tension parameter)
- Typically, when one spray nozzle is used, the stent is rotated and translated under the spray nozzle to coat all side evenly. In this configuration, one may increase the rotational speed of the stent relative to the spray nozzle. Increasing the stent rotational speed can essentially wind coating solution strands and filaments around the stent.

One of ordinary skill in the art recognizes the cumulative effect each of the above parameters has on the process. But for simplicity, each is discussed separately below. By modifying the parameters in one or more categories, a deposition process can be expected to transition from depositing a conformal polymer coating to a cobwebbed polymer coating. Relative terms such as "higher" are referenced against the typical values for the same process parameters in conformal coating processes.

Volatility Parameter

This parameter relates to the volatility, or boiling point, of the polymer solvent. Increasing the volatility of the solvent system is expected to increase the likelihood that a cobwebbed coating will form. "Solvent" in this case refers to the overall solvent composition, which can be a mixture of individual solvents. Rapid solvent evaporation during spraying leads to an increase in the viscosity of the droplets and coating on the stent. This increases the propensity for the solution to form strands that can interconnect struts.

Solvation Parameter

This parameter relates to the solubility of the polymer in the trailing solvent. As discussed above, a solvent composition dissolves the polymer for application. Once the polymer solution has been deposited onto the device, solvent begins to evaporate. But the composition of the just-evaporated solvent vapor does not match the composition of the remaining liquid solvent. Some solvent compositions will preferentially evaporate first. This means that, as the solvent evaporates, the composition of the remaining solvent smoothly changes from an initial composition to a final azeotropic composition. (An azeotropic solvent composition naturally evaporates as a single component system; i.e., it has a fixed boiling point and evaporation does not shift the composition of the remaining liquid.) This final composition is typically rich in the solvent component or components that evaporate more slowly. This solvent component, the one that evaporates more slowly than the others, is called a trailing solvent. The solvation power of this trailing solvent may be characterized by the Hildebrand solubility parameter. A solubility parameter may also be arrived at for the coating polymer. When the difference between these two solubility parameters increases, the solubility of the polymer in the solvent lessens. This trend is most applicable when the degree of hydrogen bonding of the solvent and polymer are similar. Typically, this degree of hydrogen bonding is described as high, medium, or low. Consequently, during spraying the more volatile solvent flashes off, and the polymer will tend to gel or precipitate in the trialing solvent. This gelation or precipitation prevents the formation of a smooth coating and can lead to cobwebbing.

If the polymer is less soluble in the trailing solvent versus baseline conformal-process trailing solvent, the process with poorer polymer solubility will favor polymer cobwebs.

Concentration Parameter

This parameter relates to the overall polymer concentration in the solution, usually expressed as percent solids by weight. Higher polymer concentrations versus baseline conformal-process concentrations favor polymer cobwebs. The mechanism is multifold. A higher percent solids leads to a higher solution viscosity. High viscosity solutions do not atomize as effectively into small droplets and strands or filaments can be expressed by the spray nozzle. High viscosity also stabilizes these strands so that they are long lived. Excess fluid coating on the stents surfaces can be blown off during the spray process by the force of the atomizing gas. This can further form stable strands to interconnect struts.

Spray Nozzle Temperature Parameter

This parameter relates to the temperature of the spray nozzle. Higher spray nozzle temperatures, versus baseline conformal-process temperatures favor polymer cobwebs. As coating solution is passed through the spray nozzle, it is heated to the temperature of the spray nozzle. This is advantageous compared to simply heating all of the coating solution before it enters the nozzle as the exposure time of the coating solution to the elevated temperature is short. At higher temperatures, the atomized coating solution loses solvent more rapidly. This elevates the viscosity of the coating solution favoring stand and cobweb formation. The units are temperature in ° C. of the spray nozzle.

Dry Nozzle Parameter

This parameter relates to the dry nozzle temperature. Higher dry nozzle temperatures, versus baseline conformal-process temperatures favor polymer cobwebs. When the stent moves from the spray nozzle to the drying nozzle, the action of warm convected gas removes solvent from the stent. This dries the stent and raises the temperature of the stent itself. When the stent is moved under the spray nozzle, the stent coating can absorb move solvent from the solution that is applied. The higher stent temperature also increases the evaporation rate of solvent from the stent. The drying nozzle can also elevate the temperature in the local environment, including that of the spray nozzle. These factors act to increase cobwebbing with increased dry nozzle temperature. The units are temperature in ° C. of the dry nozzle.

Flow Parameter

This parameter relates to the flow rate of the polymer solution through a spray nozzle for those processes depositing polymer from a spray. Higher flow rates versus baseline conformal-process flow rates can favor polymer cobwebs. High spray flow rates can lead to a stent coating that is very wet. This coating can flow and redistribute on the stent. Often this leads to pool webs that are regions where a continuous polymer film spans the struts at and near strut junctions. A high atomization pressure can blow this excess coating off to form strands that connect struts. The units are expressed in μg of coating applied per millimeter of stent length per second of coating time.

Atomization Pressure Parameter

This parameter relates to the atomization pressure for those processes depositing polymer from a spray. Higher atomization pressures versus baseline conformal-process atomization pressures favor polymer cobwebs. In spray coating, the atomization serves several purposes. First, it atomizes the solution into droplets. Secondly, it propels these droplets at high velocity towards the stent. And third, it significantly dries both the droplets and the coating during spraying. Drying the droplets to while they are moving towards the stent raises the percent solids of the droplets that, in turn, raise the viscosity. Higher viscosity leads to cobwebbing. Higher atomization pressure also leads to higher atomization gas flow rates and velocities. This high gas velocity past the stent can dislodge wet coating, forming strands in between the struts. In most spray coating equipment, the atomization pressure is proportional to the atomization gas velocity and is a useful indicator for the intensity of the atomization. Units are those of pressure, psi for instance.

Surface-Tension Parameter

This parameter relates to the surface tension of the polymer solution. Lower solution surface tension versus baseline conformal-process solution surface tensions favor polymer cobwebs. The formation of cobwebs increases the surface area of the polymer coating. A lower surface tension during coating favors formation of more coating surface area. It increases the stability of strands, filaments, and cobwebs while they are still fluid so that they remain after solvent removal. Units on the coating solution are those of surface tension, dyne/cm.

Stent Rotation Speed

When one spray nozzle is used, the stent rotation speed can effect the formation of cobwebbing. More rapid rotation can serve to wind the formed cobwebs and strands around the stent. Units are revolutions per minute (RPM).

One of ordinary skill will recognize that these parameters have a cumulative effect on the polymer's tendency to form cobwebs. Various embodiments comprise modifying any one of or any combination of the volatility, solubility, concentration, spray nozzle, dry nozzle, flow rate, atomization pressure, surface-tension, and rotation parameters in the direction described above to achieve polymer cobwebs. Indeed, any one or any combination of these parameters may be modified towards conformal processes (AWAY from cobweb-forming processes), if the overall deposition behavior yields polymer cobwebs. Furthermore, various embodiments are envisioned in which polymer cobwebs are formed without modifying any one of or any combination of the volatility, solubility, concentration, spray nozzle, dry nozzle, flow rate, atomization pressure, surface-tension, and rotation parameters.

A stent with a cobwebbed mesh covering made by a spray process could be used for any stenting indication. There are no limitations on the stent diameter, length, strut pattern, or strut thickness. The stent may be intended for the neurovasculature, carotid, coronary, pulmonary, aorta, renal, biliary, iliac, femoral, popliteal, or other peripheral vasculature. The stent may be balloon expandable or self-expanding.

Especially suitable materials include ductile polymers appropriate for permanent in vivo use as coatings. Elast-Eon 2 80A, a silicone urethane, has an ultimate elongation of 520% and is suitable. Other materials include polycarbonate urethanes such as Bionate and Chronoflex, silicone urethanes such as Carbosil and Purasil, polyether urethanes such as Biomer, silicones, fluorosilicates, poly(ethylene-co-vinyl alcohol), poly(ethylene-co-vinyl acetate), poly(butyl methacrylate), poly(methacrylate), poly(acrylates), styrene-ethylene/butylene-styrene triblock copolymers, styrene-isobutylene-styrene triblock copolymers, poly(vinylidene fluoride), poly(vinylidene fluoride-co-hexafluoropropylene), poly(vinylidene fluoride-co-chlorotrifluoroethylene), and solvent soluble fluoropolymers. Ethylene vinyl alcohol copolymer (commonly known by the generic name EVOH or by the trade name EVAL) is functionally a suitable choice of polymer. EVAL adheres well to the surface of a stent, particularly a stainless-steel surface, and expands on a stent without significant copolymer detachment from the surface.

Representative examples of polymer families that can be used to coat a medical device in accordance with the present invention include silicone urethanes; ABS resins; acrylic polymers and acrylic copolymers; acrylonitrile-styrene copolymers; alkyd resins; biomolecules; cellulose ethers; celluloses; copoly(ether-esters) (e.g. PEO/PLA); copolymers of polycarboxylic acids and poly-hydroxycarboxylic acids; copolymers of vinyl monomers with each other and olefins; cyanoacrylates; epoxy resins; ethylene vinyl alcohol copolymer; ethylene-methyl methacrylate copolymers; ethylene-vinyl acetate copolymers; ethylene-α-olefin copolymers; fluorosilicates; poly(acrylates); poly(amino acids); poly (anhydrides); poly(ester amides); poly(imino carbonates); poly(iminocarbonate); poly(methacrylates); poly(orthoesters); poly(tyrosine arylates); poly(tyrosine derive carbonates); polyacrylates; polyacrylic acids; polyacrylonitrile; polyalkylene oxalates; polyamides; polyamino acids; polyanhydrides; polycarbonate urethanes; polycarbonates; polycarboxylic acids; polycyanoacrylates; polydioxanones; polyester-amides; polyesters; polyether urethanes; polyethers; poly-hydroxycarboxylic acids; polyimides; polyisobutylene and ethylene-α-olefin copolymers; polyketones; polymethacrylates; polyolefins; polyorthoesters; polyoxymethylenes; polyphosphazenes; polyphosphoester urethanes; polyphosphoesters; polyphosphoesters-urethane; polyurethanes; polyvinyl alcohols; polyvinyl aromatics; polyvinyl esters; polyvinyl ethers; polyvinyl ketones; polyvinylidene halides; silicone urethanes; silicones; solvent-soluble fluoropolymers; starches; styrene-ethylene/butylenes-styrene triblock copolymers; vinyl copolymers vinyl-olefin copolymers; vinyl halide polymers and copolymers.

Representative examples of polymers that can be used to coat a medical device in accordance with the present invention include 2-hydroxyethyl methacrylate; 2-hydroxyethyl methacrylate; Biomer; Bionate; Carbosil; carboxymethyl cellulose; cellophane; cellulose; cellulose acetate; cellulose acetate butyrate; cellulose butyrate; cellulose ethers; cellulose nitrate; cellulose propionate; Chronoflex; collagen; Elast-Eon 2 80A; elastin-collagen; ethylene vinyl alcohol copolymer; fibrin; fibrinogen; hyaluronic acid; Nylon 66; poly(3-hydroxy valerate); poly(3-hydroxybutyrate); poly(4- hydroxybutyrate); poly(butyl methacrylate); poly(D,L-lactide); poly(D,L-lactide-co-glycolide); poly(D,L-lactide-co-L-lactide); poly(ethylene-co-vinyl alcohol); poly(glycolic acid); poly(glycolide); poly(hydroxybutyrate); poly(hydroxybutyrate-co-hydroxyvalerate); poly(hydroxybutyrate-co-valerate); poly(hydroxyvalerate); poly(iminocarbonate); poly(lactide-co-glycolide); poly(L-lactic acid); poly(trimethylene carbonate); polyacrylic acid; polyacrylic acid; polyacrylonitrile; polyanhydride; polyanhydride; polycaprolactam; polycaprolactone; polydioxanone; polyethylene glycol; polyisobutylene; polyisocyanate; polyorthoester; polyorthoester; polyphosphoester; polyphosphoester; polyphosphoester urethane; polyphosphoester urethane; polystyrene; polyurethane; polyvinyl acetate; polyvinyl chloride; polyvinyl esters; polyvinyl methyl ether; polyvinyl pyrrolidone; polyvinylidene chloride; polyvinylidene fluoride; Purasil; rayon; rayon-triacetate; sodium alginate; and starch.

The polymer coating for use with this invention can comprise a mixture of polymers, such as an intimate mixture of polymer molecules. Biologically active polymers are suitable, as well.

In some embodiments, the cobweb forming process operates on polymers or mixtures of polymers comprising a drug that can inhibit vascular, smooth muscle cell activity.

Useful drugs for these devices or coatings include any substance capable of exerting a therapeutic or prophylactic effect in the practice of the present invention. The drug(s) can be coated onto the polymer filaments after deposition or can be mixed into the polymer solution before deposition. These bioactive agents can be any agent that is a therapeutic, prophylactic, or diagnostic agent. These agents can have anti-proliferative or anti-inflammatory properties or can have other properties such as antineoplastic, antiplatelet, anti-coagulant, anti-fibrin, anti-thrombonic, antimitotic, antibiotic, antiallergic, antioxidant, as well as cytostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic, or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril, or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the tissues being delivered to; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Some embodiments choose the drug such that it does not contain at least one of or any combination of antiproliferative, antineoplastic, antiinflammatory, antiplatelet, anticoagulant, antifibrin, antithrombin, antimitotic, antibiotic, or antioxidant substances. Similarly, some invention embodiments choose the drug such that it does not contain one of or any combination of the drugs or drug classes listed above.

The coatings and methods of the present invention have been described with reference to a stent, such as a balloon expandable or self-expandable stent. The use of the coating is not limited to stents, however, and the coating can also be used with a variety of other medical devices. Examples of the implantable medical device that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices, such as stents, made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Methods for Coating the Device Using the Composition

The following method provides standard conformal polymer coatings. Its parameters should be modified to cause polymer cobwebbing. In some embodiments, at least one of the parameters discussed above is modified in the following process to cause the process to yield cobwebbed polymer.

After the structural members of stent 10 are formed from elastic or pseudoelastic metal, biodegradable polymer, durable polymer, or composite material, the polymeric coating can be applied to stent 10. Various methods can be used to apply the coating such as dipping, roll coating, direct application, wiping, brushing, and spraying.

The following application method is provided by way of illustration of a typical process designed to PREVENT cobwebbing and does not limit the present invention. A spray apparatus, such as EFD 780S spray device with VALVEMATE 7040 control system (manufactured by EFD Inc., East Providence, R.I.), can be used to apply a composition to stent 10. EFD 780S spray device is an air-assisted external mixing atomizer. This atomizes the composition into small droplets and uniformly applies the composition to the stent surfaces. The atomization pressure ranges from about 5 psi to about 20 psi. The droplet size depends on such factors as solution viscosity and surface tension and atomization pressure. Other types of spray applicators, including air-assisted internal mixing atomizers and ultrasonic applicators, can function to apply the composition.

Each spraying repetition can be followed by removal of some, most, or all of the solvent(s). Depending on solvent volatility, the solvent can evaporate essentially upon contact with stent 10. Alternatively, baking the stent at a mild temperature (e.g., 60° C.) for a suitable duration of time (e.g., 2-4 hours) or applying warm air can induce solvent removal. Any suitable number of repetitions can be performed to form a coating of a desired thickness or weight.

Exemplary embodiments illustrating ways to modify typical processes are shown below. A polymer composition comprising Kynar Flex 2800 can be dissolved in a solvent system comprising acetone, dioxane, and Techspray at a ratio of 25/50/25 by weight. This solution is applied to a medical device such as a stent by using a spray device such as an EFD 7805 system with VALVEMATE 7040 control system. The atomization pressure ranges from 5 psi to 25 psi.

A polymer composition comprising Solef 11010 can be dissolved in a solvent system comprising acetone, dioxane, and Techspray at a ratio of 50/25/25 by weight. This solution is applied to a medical device such as a stent by using a spray device such as an EFD 7805 system with VALVEMATE 7040 control system. The spray nozzle temperature ranges from ambient to 45° C.

A polymer composition comprising Solef 21508 can be dissolved in a solvent system comprising acetone/cyclohexanone 90/10 by weight. This solution is applied to a medical device such as a stent by using a spray device such as an EFD 7805 system with VALVEMATE 7040 control system. The dry nozzle temperature ranges from ambient to 55° C.

A polymer composition comprising Elast-Eon 2 80A can be dissolved in a solvent system comprising tetrahydrofuran/dimethylacetamide 75/25 by weight. This solution is applied to a medical device such as a stent by using a spray device such as an EFD 7805 system with VALVEMATE 7040 control system. The percent polymer solids in solution ranges from 1% to 6%.

A polymer composition comprising Kynar 710 can be dissolved in a solvent system comprising acetone/dimethylacetamide 80/20 by weight. This solution is applied to a medical device such as a stent by using a spray device such as an EFD 7805 system with VALVEMATE 7040 control system. The spray coating weight per pass ranges from 0.14 to 1.4 μg/mm sec.

After applying the composition to stent 10 and forming the polymeric coating, stent 10 can be integrated into a stent delivery system.

EXAMPLES

Example 1

A first composition was prepared by mixing the following components:
- about 2 mass % Kynar Flex 2800;
- dissolved in a mixture of acetone, dioxane, and Techspray at a weight ratio of 25/50/25

The first composition was applied onto the surface of a bare 13 mm TETRA stent (available from Guidant Corporation) by spraying and dried to form a cobwebbed stent coating. A spray coater was used, having a 0.014 round nozzle maintained at ambient temperature with a feed pressure of about 0.2 atm (about 3 psi) and an atomization pressure of about 15 psi (about 1.02 atm). The spray nozzle temperature was at ambient and a coating rate of 0.2 μg/mm sec of the wet coating was applied per pass. Between the passes, the coating was dried at using a flow of ambient temperature air for about 10 seconds. A total of 20 passes were applied. Following the last pass, the coating was baked at about 50° C. for about 2 hours. This yielded a cobwebbed, covered stent coating containing about 330 μg of Kynar Flex 2800.

Example 2

A first composition was prepared by mixing the following components:
- about 2 mass % Solef 11010;
- dissolved in a mixture of acetone, dioxane, and Techspray at a weight ratio of 50/25/25

The first composition was applied onto the surface of a bare 13 mm TETRA stent (available from Guidant Corporation) by spraying and dried to form a cobwebbed stent coating. A spray coater was used, having a 0.014 round nozzle maintained at ambient temperature with a feed pressure of about 0.2 atm (about 3 psi) and an atomization pressure of about 15 psi (about 1.02 atm). The spray nozzle temperature was at ambient and a coating rate of 0.23 μg/mm sec of the wet coating was applied per pass. Between the passes, the coating was dried at using a flow of ambient temperature air for about 10 seconds. A total of 20 passes were applied. Following the last pass, the coating was baked at about 50° C. for about 2 hours. This yielded a cobwebbed, covered stent coating containing about 347 μg of Solef 11010.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention.

Additionally, various embodiments have been described above. For convenience's sake, combinations of aspects (such as monomer type or gas flow rate) composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists in which that aspect is specifically excluded.

What is claimed is:

1. A medical device, comprising an implantable portion with cutouts in the implantable portion that create a lattice structure having sidewalls and openings, and a plurality of polymer filaments between the sidewalls or between separate portions of the same sidewall wherein the filaments have an average diameter of 0.1 to 100 microns when the device is ready for delivery and wherein the polymer filaments block 10-90 percent of an opening formed by the cutout portion.

2. The medical device of claim 1 wherein the average diameter of the filaments is 0.2 to 80 microns.

3. The medical device of claim 1 wherein the average interfilament spacing is 0.2 to 80 microns when the device is ready for delivery.

4. The medical device of claim 1 wherein the average interfilament spacing is 0.5 to 10 microns.

5. The medical device of claim 1 wherein the polymer filaments block 20-80 percent of the opening formed by the cutout portion.

6. The medical device of claim 1 wherein the polymer filaments block 30-70 percent of the opening formed by the cutout portion.

7. The medical device of claim 6 wherein the medical device is a stent.

8. A method comprising inserting the medical device of claim 1 into a body lumen at a treatment position.

9. The method of claim 8 wherein the medical device is a stent.

10. The method of claim 9 wherein the filaments additionally comprise drug(s).

11. The method of claim 10 wherein the drug is selected from the group consisting of an antiproliferative, an antineoplastic, an antiinflammatory, an antiplatelet, an anticoagulant, an antifibrin, an antithrombin, an antimitotic, an antibiotic, an antioxidant and combinations thereof.

12. The method of claim 8 wherein the polymer filaments are selected from the group consisting of Elast-Eon 2 80A, polycarbonate urethanes, silicone urethanes, polyether urethanes, silicones, fluorosilicates, poly(ethylene-co-vinyl alcohol), poly(ethylene-co-vinyl acetate), poly(butyl methacrylate), poly(methacrylate), poly(acrylates), styrene-ethylene/butylene-styrene triblock copolymers, styrene-isobutylene-styrene triblock copolymers, poly(vinylidene fluoride), poly(vinylidene fluoride-co-hexafluoropropylene), poly(vinylidene fluoride-co-chlorotrifluoroethylene), and solvent soluble fluoropolymers.

13. A method of making the medical device of claim 6 comprising coating a medical device with a composition comprising a polymer wherein the step of coating comprises selecting any combination of process parameters such that polymer filaments form between the sidewalls.

14. The medical device of claim 1 wherein the medical device is a stent.

15. The medical device of claim 14 wherein the filaments additionally comprise drug(s).

16. The medical device of claim 15 wherein the drug is selected from antiproliferative, antineoplastic, antiinflammatory, antiplatelet, anticoagulant, antifibrin, antithrombin, antimitotic, antibiotic, or antioxidant substances, or their combinations.

17. The medical device of claim 14 wherein the polymer is selected from Elast-Eon 2 80A, polycarbonate urethanes, silicone urethanes, polyether urethanes, silicones, fluorosilicates, poly(ethylene-co-vinyl alcohol), poly(ethylene-co-vinyl acetate), poly(butyl methacrylate), poly(methacrylate), poly(acrylates), styrene-ethylene/butylene-styrene triblock copolymers, styrene-isobutylene-styrene triblock copolymers, poly(vinylidene fluoride), poly(vinylidene fluoride-co-hexafluoropropylene), poly(vinylidene fluoride-co-chlorotrifluoroethylene), and solvent soluble fluoropolymers.

18. A method of making the medical device of claim 1 comprising coating a medical device with a composition comprising a polymer wherein the step of coating comprises selecting any combination of process parameters such that polymer filaments form between the sidewalls.

* * * * *